(12) United States Patent
Bjerregaard et al.

(10) Patent No.: US 11,383,022 B2
(45) Date of Patent: Jul. 12, 2022

(54) NOZZLE FOR AN ENEMA DEVICE, A PACKAGING INCLUDING THE NOZZLE, AND AN ENEMA DEVICE COMPRISING THE NOZZLE

(71) Applicant: MBH-INTERNATIONAL A/S, Allerød (DK)

(72) Inventors: Henrik Bork Bjerregaard, Brønshøj (DK); Cathrine Ørsnes Due, Holte (DK); Thit Rosen Hagen, Roskilde (DK)

(73) Assignee: MBH-INTERNATIONAL A/S, Allerød (DK)

( * ) Notice: Subject to any disclaimer, the term of this patent is extended or adjusted under 35 U.S.C. 154(b) by 243 days.

(21) Appl. No.: 16/348,136

(22) PCT Filed: Nov. 2, 2017

(86) PCT No.: PCT/DK2017/050361
§ 371 (c)(1),
(2) Date: May 7, 2019

(87) PCT Pub. No.: WO2018/086664
PCT Pub. Date: May 17, 2018

(65) Prior Publication Data
US 2019/0275232 A1    Sep. 12, 2019

(30) Foreign Application Priority Data
Nov. 8, 2016   (DK) .......................... PA 2016 70877

(51) Int. Cl.
*A61M 3/02* (2006.01)
*B65D 51/18* (2006.01)

(52) U.S. Cl.
CPC ........... *A61M 3/0279* (2013.01); *B65D 51/18* (2013.01); *A61M 2205/0222* (2013.01);
(Continued)

(58) Field of Classification Search
CPC ........ A61M 3/0279; A61M 2205/0222; A61M 2205/0238; A61M 2207/00;
(Continued)

(56) References Cited

U.S. PATENT DOCUMENTS 1,072,467 A * 9/1913 James ................. A61M 3/0279
604/278
2,176,391 A * 10/1939 Chalmers ............ A61M 3/0287
604/41

(Continued)

FOREIGN PATENT DOCUMENTS

CA      2673750 A    7/2008
EP     1011754 A1    6/2000
(Continued)

OTHER PUBLICATIONS

International Search Report and Written Opinion, Appl. No. PCT/DK2017/050361, dated Feb. 12, 2018.
(Continued)

*Primary Examiner* — J. Gregory Pickett
*Assistant Examiner* — Jenine Pagan
(74) *Attorney, Agent, or Firm* — Fox Rothschild LLP

(57) ABSTRACT

A funnel-shaped enema nozzle (1) that includes a flared proximal part (2) that tapers into a tubular distal part (3), has at least a part of an exterior annular wall (3a) of the tubular distal part (3) provided with a hydrophilic coating (4) to provide reduced friction during use of the nozzle (1) during performing an enema.

24 Claims, 2 Drawing Sheets

(52) U.S. Cl.
CPC . *A61M 2205/0238* (2013.01); *A61M 2207/00* (2013.01); *A61M 2209/06* (2013.01); *B65D 2251/0018* (2013.01); *B65D 2251/0093* (2013.01)

(58) Field of Classification Search
CPC ............... A61M 2209/06; B65D 51/18; B65D 2251/0018; B65D 2251/0093
USPC ....... 206/570, 571, 205, 207, 210, 572, 364; 604/257, 275
See application file for complete search history.

(56) References Cited

U.S. PATENT DOCUMENTS

| | | | | |
|---|---|---|---|---|
| 3,428,046 | A * | 2/1969 | Vagenius | A61L 29/043 604/265 |
| 4,004,589 | A | 1/1977 | Neumeier | |
| 4,301,798 | A * | 11/1981 | Anderson | A61M 3/0283 604/278 |
| 5,578,017 | A * | 11/1996 | Aguilar | A61M 3/0279 604/275 |
| 6,210,381 | B1 * | 4/2001 | Morse | A61M 3/0279 604/289 |
| 6,527,752 | B1 * | 3/2003 | Bosley, Jr. | A61B 17/43 604/264 |
| 2001/0001443 | A1 * | 5/2001 | Kayerod | A61M 25/002 206/364 |
| 2006/0163097 | A1 * | 7/2006 | Murray | B65B 5/04 206/364 |
| 2006/0263404 | A1 * | 11/2006 | Nielsen | A61M 25/0045 424/422 |
| 2008/0243090 | A1 * | 10/2008 | Tsai | A61M 3/0279 604/261 |
| 2009/0192448 | A1 | 7/2009 | Talamonti | |
| 2019/0231969 | A1 * | 8/2019 | Hougaard | A61M 25/0009 |

FOREIGN PATENT DOCUMENTS

| | | |
|---|---|---|
| EP | 1404403 A2 | 4/2004 |
| GB | 2527278 A | 12/2015 |

OTHER PUBLICATIONS

Written Opinion of the International Preliminary Examining Authority, Appl. No. PCT/DK2017/050361, dated Aug. 9, 2018.
International Preliminary Report on Patentability, Appl. No. PCT/DK2017050361, dated Nov. 8, 2018.

* cited by examiner

NOZZLE FOR AN ENEMA DEVICE, A
PACKAGING INCLUDING THE NOZZLE,
AND AN ENEMA DEVICE COMPRISING
THE NOZZLE

This application is a 371 filing of International Patent Application PCT/DK2017/050361 filed Nov. 2, 2017, which claims priority to application no. PA 2016 70877 filed Nov. 8, 2016.

TECHNICAL FIELD

The present invention relates to a funnel-shaped enema nozzle of the kind comprising a flared proximal part that tapers into a tubular distal part, in particular a nozzle for an irrigation apparatus or an enema device.

BACKGROUND

Administrating an enema is a common procedure whereby liquid is injected into the rectum and lower intestine of a patient in order to induce bowel movement. The need for such a procedure typically arises in patients suffering from certain physical ailments in which voluntary bowel control is impaired or when the bowel needs to be cleaned before e.g. a coloscopy or a surgical operation. Typically irrigation and enema is however performed to motivate evacuation of stool, to relieve constipation, avoid or treat faecal incontinence, or just for cleansing the intestinal duct when desired.

Moreover, enemas are often administered to a patient at home when the need for medical assistance does not necessitate a doctor or another health care assistant. However, it is often difficult for the patient to administer the enema to him or herself since the applicator nozzle must be inserted into such a small, sensitive area, either via the anus or a stoma, or inserted into a fistula. Frequent use may however cause inconveniences, such as induce microtrauma.

The risk that the applicator nozzle pops out and of leakage is also a great concern during enema procedures. Moreover, it is difficult for the patient to administer the liquid while steadily holding the enema in the required area. Often the patient is assisted by another individual; however, assistance may not always be available, if, for instance, the patient lives alone.

The applicant's international patent application no. PCT/IB2010/051818 discloses a conical nozzle of the kind mentioned in the opening paragraph. This known nozzle needs however application of a lubricant in order to reduce frictional force when inserting the nozzle in the rectum or other body cavity to be cleansed or irrigated. Although lubrication is an effective means to reduce friction the user or patient must apply the lubricant thereby soiling the finger, the lubricant is often runny and dripping is difficult to avoid, and for the patient annoying residues of lubricant remains both inside and outside the body around and at the site of use, and these residues must be removed in order not to soil the clothes.

SUMMARY OF THE INVENTION

British patent application no. GB 2527278 A relates to an insertion device for an irrigation system comprising a positioning collar and a hollow shaft having. The insertion device has a hydrophilic coating. A stepped adaptor protrudes from the positioning collar at the base of the hollow shaft to facilitate connection with a conduit to allow a liquid to he introduced into the insertion device.

Canadian patent application no. CA 2673750 A1 discloses an irrigation system with a transanal insertion member provided with a hydrophilic coating. A liquid tube for holding and/or conducting liquids fluidly connects a liquid reservoir with the insertion member. The liquid reservoir and the insertion member is permanently fastened to the liquid tube.

Therefore, it is a main aspect of the present invention to provide a nozzle for an enema device of the kind mentioned in the opening paragraph that can be used without application of lubrication.

It is yet an aspect of the present invention to provide a nozzle for an enema device of the kind mentioned in the opening paragraph that effectively can administer a liquid, e.g. an enema or other liquid solution, to a patient without causing discomfort.

It is yet an aspect of the present invention to provide a nozzle for an enema device of the kind mentioned in the opening paragraph that prevents backflow and leakage of liquid after and during use.

It is yet an aspect of the present invention to provide a nozzle for an enema device of the kind mentioned in the opening paragraph that is inexpensive to manufacture and is simple and reliable to use.

It is yet an aspect of the present invention to provide a nozzle for an enema device of the kind mentioned in the opening paragraph that is relatively small and easy to operate, especially by one hand.

It is yet an aspect of the present invention to provide a nozzle for an enema device of the kind mentioned in the opening paragraph that reduces risk of causing microtrauma.

It is yet an aspect of the present invention to provide a nozzle for an enema device of the kind mentioned in the opening paragraph that can be packaged ready for use.

The novel and unique whereby these and other aspects are achieved consist in that at least a part of an exterior annular wall of the tubular distal part has a hydrophilic coating.

Nozzles having substantially the same diameter along the entire length, thus nozzles not having a flared proximal part, and nozzles in general not having an overall conical appearance are not part of the present invention.

In a preferred embodiment the entire circumference and length of the exterior wall of the tubular distal part can have a continuous or discontinuous hydrophilic coating, for example either as a full coverage coating or an island coating consisting of hydrophilic dots separated by not-coated areas.

When the hydrophilic coating gets wet, e.g. simply when contacted with water, saline or other liquid swelling medium prior to inserting the funnel-shaped enema nozzle, the hydrophilic coating gels and/or swells and confers a friction-reducing surface to the exterior face of the coated section or coated part of at least the tubular distal part of the funnel-shaped enema nozzle, thereby enabling a gentle insertion of said tubular distal part into e.g. the rectum. Once the tubular distal part is inserted and in contact with the mucosal surface liquid, which is expelled through the tubular distal part, becomes a liquid head in front of the tubular distal part that substantially plugs the rectum or other relevant duct. The swelled hydrophilic coating is resilient and flexible and this property, together with the remaining liquid absorbing properties of the hydrophilic coating, makes the hydrophilic coating also act as an effective seal against leakage along the length of the tubular distal part and out of the rectum or other body cavity.

The hydrophilic coating advantageously reduces the risk of injuring the adjacent tissue, such as inducing microtrauma, i.e. microtearing of e.g. the muscle fibres, the sheath around the muscle, mucosal tissue and the connective tissue in the rectum and at the anus. Microtrauma, macrotrauma and other kinds of tissue trauma in general may also cause inflammation and pain. Repetitive tissue trauma, which are not allowed time to heal, can result in more serious conditions and the funnel-shaped enema nozzle having a hydrophilic coating expediently reduces this risk. Repetitive enemas can be done without concerns to trauma to surrounding tissue.

The need to reduce friction outside the body is normally not similarly relevant. However, some patients that need frequent irrigation and use of enemas may however suffer from redness, irritation, excoriation and even open sores at the site of insertion, such as around the anus or around a stoma. Such patients may benefit from a funnel-shaped enema nozzle also having a hydrophilic coating at least at a part of the face of the annular wall of the flared proximal part as well.

The tubular distal part conveniently has an outlet opening for expelling the liquid and a tubular coupling piece for coupling to a source of liquid for use in irrigation or enema, which coupling piece has an inlet opening and being surrounded by the flared proximal part to be easily accessed by the user.

In order not to injure the body cavity during insertion of the tubular distal part, the edge of the outlet opening of the tubular distal part may advantageously be rounded.

At least a part of the exterior wall of the funnel-shaped enema nozzle may be uneven. Preferably at least a part of the exterior face of the flared proximal part is uneven.

The uneven part of the exterior wall of the funnel-shaped enema nozzle, such as of the flared proximal part, may advantageously have a surface roughness of between 2.0-3.0 $R_a$, preferably 2.8 $R_a$ obtained by abrasive blasting of a corresponding mold cavity part.

A preferred material for manufacturing of the funnel-shaped enema nozzle of the present invention is polyurethane (PU), which however tend to cling to some packaging materials which complicates the packing process. The uneven surface allows the funnel-shaped enema nozzle to easily be put into a plastic bag after manufacturing. Such packaging is subsequent sealed for storage but after use of the funnel-shaped enema nozzle the same packaging can be used for its disposal. Other kinds of plastic polymers, such as polyethylene (PE) and polyvinyl chloride (PVC) for manufacturing the funnel-shaped enema nozzle may pose similar packaging problems, or different packaging problems, such as static electricity and other kinds of attraction between packaging material and nozzle material. The funnel-shaped enema nozzle can also be manufactured of silicone, styrene ethylene butylene styrene (SEBS), thermoplastic polyester elastomer (TPC), thermoplastic styrenic elastomer (TPS), and other flexible elastomeric polymers.

A further advantage is that the uneven surface facilitates release of the funnel-shaped enema nozzle from the mold cavities.

The desired roughness can e.g. be obtained by abrasive blasting of the corresponding mold cavity part, e.g. a moderately abrasive blasting such as glass bead blasting, where the profile roughness parameter $R_a$ is the arithmetic average of the absolute values and being defined by $$R_a = \frac{1}{n}\sum_{i=1}^{n}|y_i|$$

which roughness profile contains n ordered, equally spaced points along a defined trace, and $y_i$ is the vertical distance from a mean line to the $i^{th}$ data point. Height is assumed to be positive in the up direction, away from the bulk material of the mold cavity part.

The exterior surface of the wall of the tubular distal part may e.g. have a surface roughness $R_a$ below 0.5 $R_a$, preferably below 0.3 $R_a$, more preferred below 0.1 $R_a$, and even more preferred $R_a$=0. Such surface quality can e.g. be obtained by polishing a corresponding mold cavity part to provide this aforesaid exterior surface with as smooth a surface as possible and so that the patient is not injured when using the funnel-shaped nozzle.

Any of the abrasive blasting and polishing can then be done prior to the coating step with the hydrophilic coating.

The funnel-shaped enema nozzle of the present invention has a compact design, which is easy to use. For example the exterior diameter of the flared proximal part may be about at least 50% larger than the exterior diameter of the tubular distal part at the outlet opening, however it might be preferably that the exterior diameter of the flared proximal part is about at least 60% larger than the exterior diameter of the tubular distal part at the outlet opening, and more preferred about at least 70% larger than the exterior diameter of the tubular distal part at the outlet opening.

Enema nozzles are made in several different sizes and shapes and materials. According to www.enema-web.com/enema_nozzle.htm a standard enema nozzle for an adult is approximately 9 cm long and 0.65 cm in diameter and has no flared proximal part.

For the funnel-shaped enema nozzle of the present invention
- the axial length of the funnel-shaped enema nozzle can be between 1.2 and 1.5 times larger than the exterior diameter of the flared proximal part, preferably 1.25 times larger, and/or
- the exterior diameter of the tubular coupling piece at the transition of the tubular distal part into the flared proximal part can be larger than the exterior diameter of the tubular coupling piece at the inlet opening, and/or the axial length of the tubular distal part including the tubular coupling piece may be substantially the same as the exterior diameter of the flared proximal part.

The tubular coupling piece may have a length of e.g. half the axial length of the flared proximal part. Preferably the axial length of the funnel-shaped enema nozzle is between 45-95 mm.

Preferably the tubular coupling piece can be elastic and/or flexible to facilitate mating with another coupling piece to establish liquid communication to the source of irrigation or enema liquid, e.g. as described in the applicant's international patent application no. PCT/IB2010/051818.

The tubular coupling piece may either be a plastic tube inserted and secured at least a distance into the tubular distal part at the transition between the tubular distal part and the flared proximal part. The tubular coupling piece can e.g. be secured by means of gluing, or the tubular coupling piece can be made as an integral part of the funnel-shaped enema nozzle by using multi-component injection molding.

The present invention further relates to a packaging including the funnel-shaped enema nozzle described above and a liquid in liquid contact with the hydrophilic coating so that the hydrophilic coating is already ready for use at the moment it is taken out of the packaging. There is thus no need to contact the nozzle with water to make it swell to reach the friction-reducing level.

Advantageously the packaging is made of a material that prevents evaporation of more than 10% of the liquid from the packaging during a year of storage. Such a material can e.g. be a laminate of metal foil, e.g. aluminium, and a plastic film, e.g. one or more film layers of a thermoplastic film, such as polyethylene or polyvinyl chloride. Preferably the material of the packaging prevents evaporation of more than 5% of the liquid from the packaging during a year of storage, and even more preferred the material of the packaging prevents evaporation of more than 1% of the liquid, wherein the wet storage temperature preferably is below or equal to room temperature, such as below or equal to 25° C. The wet-packaged funnel-shaped enema nozzle can be cold packed, e.g. at a temperature of about 4° C.-10° C.

In a preferred embodiment the packaging prevents evaporation of so little liquid at all that the swelling properties are maintained during up to two years of storage at room temperature to make sure that the funnel-shaped enema nozzle does not loose the friction-reducing property during storage, and so that the wet, swelled hydrophilic coating is not at risk of clinging to the packaging and attach to said packing when taken out. Materials of film and foil layer layers can vary, and so can thickness of such layers. Thickness can e.g. be between 10 µm-100 µm, e.g. 20 µm-50 µm. Also the overall design of the packaging can vary.

The packaging may advantageously be made by welding two sheets of packaging material together, be bag-shaped, pouch-shaped, cup-shaped and sealed with a cover, or combinations of these and other packaging designs. Oversize packaging is also possible to make sure that the funnel-shaped enema nozzle and other parts of the enema device, which has been contaminated with faeces and bacteria, can be disposed all together.

A cup-shaped embodiment of a packaging can advantageously in addition have a detachable lid, which the user of the funnel-shaped enema nozzle can use to close the cup-shaped packaging after a used and soiled funnel-shaped enema nozzle has been placed inside it. The cup-shaped embodiment of a packaging can thus also serve as a convenient receptacle for disposal of a used funnel-shaped enema nozzle.

Accordingly, the funnel-shaped enema nozzle of the present invention can be provided to the user in a wet ready to use state, or in dry state to be wetted by the user prior to use to make the hydrophilic coating swell into a soft layer that will serve as a friction-reducing interface between tissue and nozzle part when the funnel-shaped enema nozzle is inserted into a certain body cavity to achieve the friction-reducing property.

If the packaging is used to dispose a used funnel-shaped enema nozzle additional closure and/or sealing means or mechanisms can be part of the packaging, such as e.g. a lid for the cup-shaped embodiment of a packaging, or twist ties for at a more flat pouch-shaped version of the packaging.

The packaging is preferably made of a material that is smell-tight and/or bacteria impermeable and the closure and/or sealing means or mechanisms be selected and configured with similar properties.

An exemplary hydrophilic coating can be made of polyvinylpyrrolidone (PVP) or other hydrophilic or predominately hydrophilic polymers.

The present invention further relates to a nozzle assembly comprising the funnel-shaped enema nozzle, a packaging adapted for containing the funnel-shaped enema nozzle, and a liquid contained inside the packaging and being in liquid contact with the hydrophilic coating of the funnel-shaped enema nozzle.

BRIEF DESCRIPTION OF THE DRAWINGS

The invention will now be described in further details by way of an exemplary embodiment with reference to the drawing, in which.

DETAILED DESCRIPTION OF THE INVENTION

Figure 1:
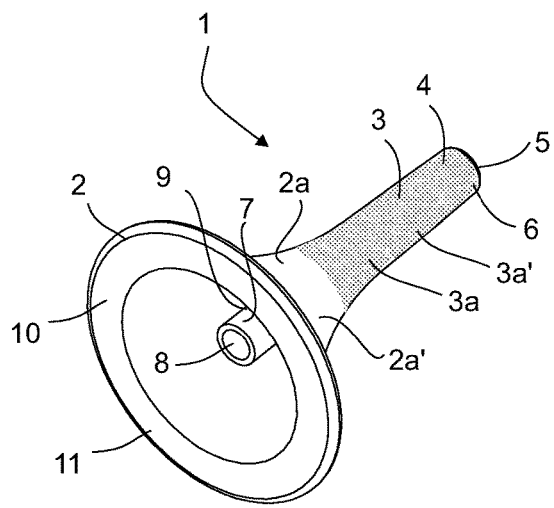
FIG. 1 is a perspective view of a funnel-shaped enema nozzle seen from the flared proximal part.

In the exemplary embodiment of a funnel-shaped enema nozzle shown in the drawing and described below the entire tubular distal part has a hydrophilic coating. This exemplary embodiment is not exhaustive for positioning the hydrophilic coating on the exterior face of the funnel-shaped enema nozzle. As already mentioned above more or less of the exterior face of the funnel-shaped enema nozzle can be covered with hydrophilic coating and this hydrophilic coating can be both continuous and discontinuous, such as a pattern of hydrophilic dots. Furthermore, also more or less of the exterior face of the flared proximal part of the funnel-shaped enema nozzle can have a hydrophilic coating. Below the funnel-shaped enema nozzle of the present invention is for simplicity referred to as "the nozzle".

Figure 2:
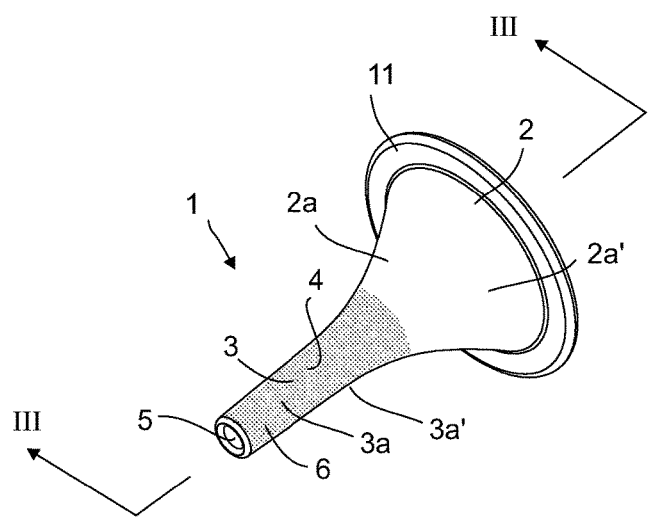
FIG. 2 shows the same seen from the tubular distal part.

The nozzle 1 shown in FIGS. 1 and 2 has a flared proximal part 2 that tapers into a tubular distal part 3. The flared proximal part 2 has a proximal annular wall 2a with an exterior proximal face 2a' without a hydrophilic coating, and the tubular distal part 3 has a distal annular wall 3a with an exterior distal face 3a' with a hydrophilic coating 4.

The tubular distal part 3 has an outlet opening 5 for enema liquid at a distal end 6 and an elastic tubular coupling piece 7 with an inlet opening 8 at a proximal opposite end 9. The elastic tubular coupling piece 7 is surrounded by the flared proximal part 2.

In the present embodiment of a nozzle 1 the flared proximal part 2 has a circumferential radial protrusion 10, that serve as a grasping flange 11 to facilitate insertion and withdrawal of the nozzle 1. Thus the grasping flange 11, although not mandatory, facilitates convenient operation of the nozzle 1.

Figure 3:
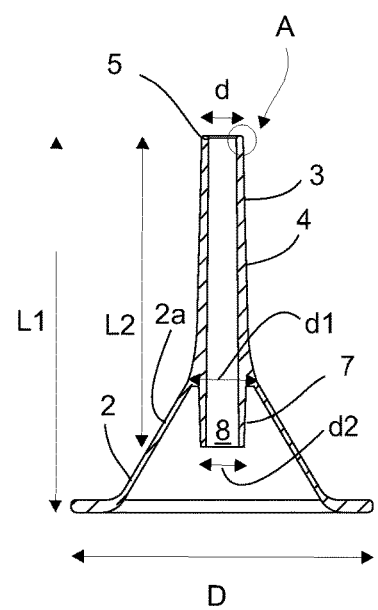
FIG. 3 is a longitudinal sectional view taken along line III-III in FIG. 2.

The longitudinal sectional view of FIG. 3 illustrates that for the present embodiment the tubular coupling piece 7 does not protrude outside the flared proximal part 3.

For the present exemplary embodiment the exterior diameter D of the flared proximal part 2 at the grasping flange 11 is smaller than both the total length L1 of the nozzle 1 and smaller than the length L2 between the inlet opening 8 and the outlet opening 5. The exterior diameter d of tubular distal part 3 at the inlet opening 8 is substantially smaller than the exterior diameter D of the flared proximal part 2 of the flared proximal part 2. The exterior diameter d1 of the tubular coupling piece at the transition of the tubular distal part 3 into the flared proximal part 2 is larger than the exterior diameter d2 of the tubular coupling piece 7 at the inlet opening 8.

Figure 4:
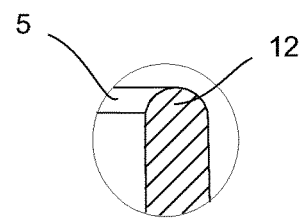
FIG. 4 is a fragmentary view of the encircled area A of FIG. 3.

As can be seen in the enlarged scale view of FIG. 4 of the detail A of FIG. 3 the circumferential wall of the tubular distal part 3 at the outlet opening 5 has a rounded end 12 to avoid injuring the intestinal wall during insertion and withdrawal of the nozzle 1.

Figure 5:
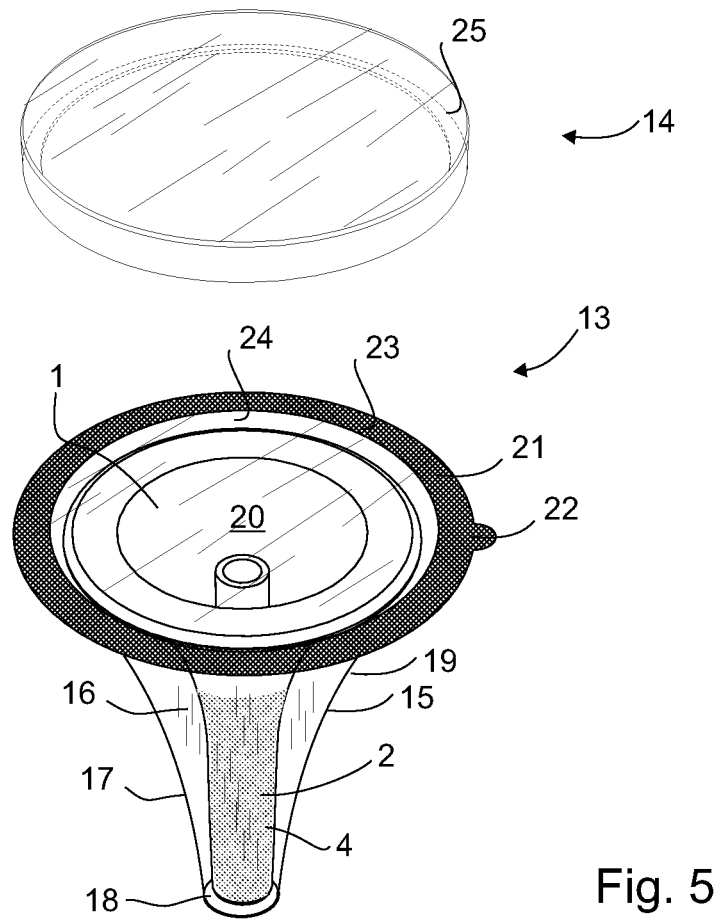
FIG. 5 shows a perspective view of a first embodiment of a packaging in form of cup-shaped packaging with a separate lid.

FIG. 5 is a perspective view of a first embodiment of a packaging in form of cup-shaped packaging 13 with a separate lid 14. Both the cup-shaped packaging 13 and the lid 14 are for illustrative purposes shown to be transparent.

The cup-shaped packaging 13 has a cup part 15 for accommodating both the funnel-shaped enema nozzle 1 and a liquid 16 in contact with the hydrophilic coating 4 inside the cup part 15 to make said coating 4 swells and be friction-reducing. The cup part 15 is tapered, thus substantial conical, similarly to the funnel-shaped enema nozzle 1, and has a tapered protective part 17, which is closed at the bottom 18 and serves for protecting the swelled hydrophilic coating 4 at the tubular distal part 2. Opposite the bottom 18 the tapered protective part 17 widens into a conical part 19 with an insertion opening 20 for the funnel-shaped enema nozzle 1. This cup-shaped packaging design prevents the user from touching the ready to use funnel-shaped enema nozzle 1 when it is taken out of the packaging 13. The insertion opening 20 is covered with a gas-impermeable removable cover 21, e.g. a metal foil cover similarly to the lid of a dairy product cup.

The cover 21 can e.g. be heat-sealed to a sealing flange 23 along the perimeter 24 of the insertion opening 20 of the cup-shaped packaging 13, and the lid 14 be used to cover and close around the insertion opening 20 afterwards when the removable cover 21 has been taken off. The removable cover 21 has a grasping flap 22 to facilitate easy removal.

The lid 14 has a coupling flange 25 configured to snap below the sealing flange 23 to intimately close the insertion opening 20, preferably to close the cup-shaped packaging 13 with the contaminated funnel-shaped enema nozzle 1 in a gas-impermeable, liquid-tight, bacteria-tight and/or odor free condition.

Figure 6:
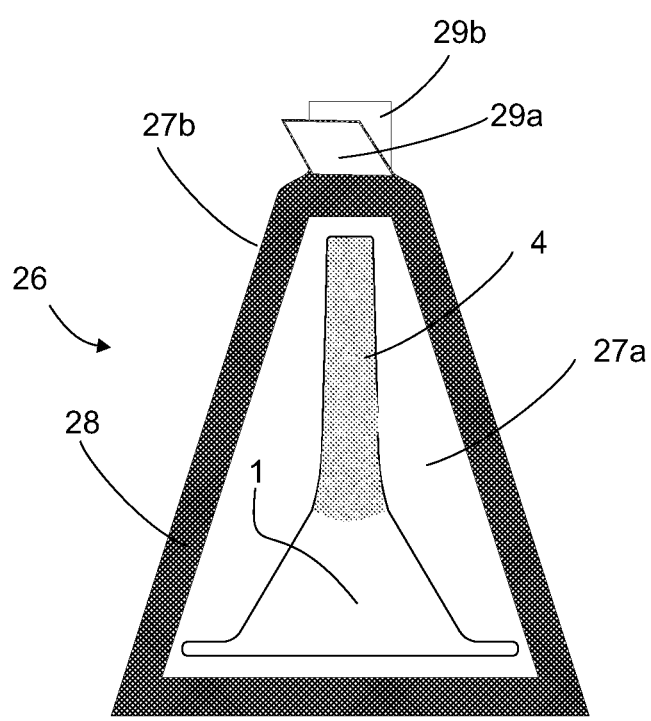
FIG. 6 shows, schematically seen from the side, a second embodiment of a packaging.

FIG. 6 shows schematically, seen from the side, a second embodiment of a transparent packaging 26 without liquid content. Thus the funnel-shaped enema nozzle 1 is not immediate ready for use, but needs wetting prior to use. The packaging 26 is made of opposite sheets 27a,27b of one or more layers or films of e.g. plastic materials, metal enforced plastic material, or simply paper, or combination of layers of the aforesaid materials, which sheets 27a,27b are glued or heat-welded together along an exterior outline 28 leaving opposite flaps 29a,29b of each of the opposite sheets 27a, 27b free of mutual attachment to serve to easy separate the opposite sheets 27a,27b to open the second embodiment of a packaging 26 in order to take the funnel-shaped enema nozzle 1 out of the packaging 26.

Transparency of the packaging is not mandatory and less preferred for embodiments where the packaging is also used for disposal of the nozzle after use. Thus emphasis is made that since both the above examples of designs of packaging can be used as a receptacle for disposal of the funnel-shaped enema nozzle after use, a more aesthetic packaging may not be transparent, or just partly transparent.

The funnel-shaped enema nozzle 1 of the present invention may be disposable or reusable as desired. In particular, for some inexpensive embodiments the hydrophilic coating 4 may loose adherence to the nozzle and detach when retracted after use, in which case the funnel-shaped enema nozzle 1 cannot be used again. However in other embodiments the hydrophilic coating 4 of the funnel-shaped enema nozzle 1 can be washed and store wet, or be dried and rewetted anew, in which cases the funnel-shaped enema nozzle 1 is for reuse, at least a couple of times.

What is claimed is:

1. A funnel-shaped enema nozzle (1) comprising a flared proximal part (2) that tapers into a tubular distal part (3) that has an outlet opening (5) at a distal end (6), at least a part of an exterior annular wall of the tubular distal part (3) has a hydrophilic coating (4), wherein the tubular distal part (3) has an elastic or flexible tubular coupling piece (7) with an inlet opening (8) at a proximal opposite end (9), which tubular coupling piece (7) is surrounded by the flared proximal part (2) and does not protrude outside the flared proximal part (2), and wherein an exterior diameter (D) of the flared proximal part (2) increases continuously towards the proximal opposite end (9).

2. The funnel-shaped enema nozzle (1) according to claim 1, wherein the entire exterior wall (3a) of the tubular distal part (3) has a hydrophilic coating (4).

3. The funnel-shaped enema nozzle (1) according to claim 1, wherein at least a part of the exterior wall (2a) of the flared proximal part (2) has a hydraulic coating (4).

4. The funnel-shaped enema nozzle (1) according to claim 1, wherein an annular edge (12) of the outlet opening (5) of the tubular distal part (3) is rounded.

5. The funnel-shaped enema nozzle (1) according to claim 1, wherein at least a part of an exterior wall (2a;3a) of the funnel-shaped enema nozzle (1) is uneven.

6. The funnel-shaped enema nozzle (1) according to claim 5, wherein the uneven part of the exterior wall (2a;3a) of the funnel-shaped enema nozzle (1) is the exterior wall (2a) of the flared proximal part (2) of the funnel-shaped enema nozzle (1).

7. The funnel-shaped enema nozzle (1) according to claim 5, wherein a surface roughness of the uneven part of the funnel-shaped enema nozzle (1) is between 2.0-3.0 Ra or is 2.8 Ra.

8. The funnel-shaped enema nozzle (1) according to claim 5, wherein the funnel-shaped enema nozzle (1) is manufactured by molding in a mold having a mold cavity part with a surface corresponding to the uneven part of the nozzle (1), which surface is uneven by abrasive blasting.

9. The funnel-shaped enema nozzle (1) according to claim 1, wherein at least a part of the exterior wall (3a) of the tubular distal part (3) is smooth.

10. The funnel-shaped enema nozzle (1) according to claim 9, wherein the funnel-shaped enema nozzle is manufactured by molding in mold having a mold cavity part with a surface corresponding to the smooth part of the nozzle (1), which surface is smooth by polishing.

11. The funnel-shaped enema nozzle (1) according to claim 9, wherein the smooth part of the exterior wall (3a) of the tubular distal part (3) has a surface roughness which is either below 0.5 Ra, below 0.3 Ra, or below 0.1 Ra, or Ra is substantially 0.

12. The funnel-shaped enema nozzle (1) according to claim 1, wherein the exterior diameter (D) of the flared proximal part (2) is either about at least 50% larger than the exterior diameter (d) of the tubular distal part (3) at the outlet opening (5), at least 60% larger than the exterior diameter (d) of the tubular distal part (3) at the outlet opening (5), or about at least 70% larger than the exterior diameter (d) of the tubular distal part (3) at the outlet opening (5).

13. The funnel-shaped enema nozzle (1) according claim 1, wherein an axial length (L1) of the funnel-shaped enema nozzle (1) is either between 1.2 and 1.5 times larger than the exterior diameter (D) of the flared proximal part (2), or is 1.25 times larger.

14. The funnel-shaped enema nozzle (1) according to claim 1, wherein the axial length (L1) of the funnel-shaped enema nozzle (1) is between 45-95 mm.

15. The funnel-shaped enema nozzle (1) according to claim 1, wherein an exterior diameter (d1) of the tubular coupling piece (7) at the transition of the tubular distal part (3) into the flared proximal part (2) is larger than the exterior diameter (d2) of the tubular coupling piece (7) at the inlet opening (8).

16. The funnel-shaped enema nozzle (1) according to claim 1, wherein the tubular coupling piece (7) is a plastic tube inserted at least a distance into the tubular distal part (3) via the transition opening between the tubular distal part (3) and the flared proximal part (2).

17. The funnel-shaped enema nozzle (1) according to claim 1, wherein the hydrophilic coating (4) is a polyvinylpyrrolidone coating.

18. A packaging (13;26) including the funnel-shaped enema nozzle (1) according to claim 1 and a liquid (16) in liquid contact with the hydrophilic coating (4).

19. The packaging (13;26) according to claim 18, wherein the packaging (13;26) is made of a material that either prevents evaporation of more than 10% of the liquid (16) from the packaging (13;26) during a year of storage, more than 5% of the liquid (16) from the packaging (13;26) during a year of storage, or more than 1% of the liquid (16) from the packaging (13;26) during a year of storage, or no liquid (16) evaporates from the packaging (13;26) during a year of storage.

20. The packaging (13;26) according to claim 18, wherein the packaging (13;26) is made of a material that is smell-tight or bacteria impermeable.

21. The packaging (13) according to claim 18, wherein the packaging (13;26) comprises a lid (14).

22. A nozzle assembly comprising the funnel-shaped enema nozzle (1) according to claim 1, a packaging (13;26) adapted for containing the funnel-shaped enema nozzle (1), and a liquid (16) contained inside the packaging (13;26) and being in liquid contact with the hydrophilic coating (4) of the funnel-shaped enema nozzle (1).

23. The nozzle assembly according to claim 22, wherein the packaging (13;26) comprises a lid (14).

24. An enema device comprising a flared proximal part (2) that tapers into a tubular distal part (3) that has an outlet opening (5) at a distal end (6), at least a part of an exterior annular wall of the tubular distal part (3) has a hydrophilic coating (4), wherein the tubular distal part (3) has an elastic or flexible tubular coupling piece (7) with an inlet opening (8) at a proximal opposite end (9), which tubular coupling piece (7) is surrounded by the flared proximal part (2) and does not protrude outside the flared proximal part (2), and wherein a diameter of the flared proximal part (2) increases continuously towards the proximal opposite end (9).

\* \* \* \* \*